United States Patent [19]

Ohno et al.

[11] 3,957,523

[45] May 18, 1976

[54] COATING COMPOSITIONS FOR SOLID MEDICINES

[75] Inventors: Shigeru Ohno, Kamakura; Noboru Hoshi, Tokorozawa; Fujio Sekigawa, Yono, all of Japan

[73] Assignee: Shinetsu Chemical Company, Tokyo, Japan

[22] Filed: Mar. 28, 1974

[21] Appl. No.: 455,533

[30] Foreign Application Priority Data

Apr. 2, 1973  Japan.............................. 48-36638

[52] U.S. Cl................................ 106/189; 106/196; 106/197 C; 424/362
[51] Int. Cl.² ...................... C08L 1/12; C08L 1/26
[58] Field of Search..................... 424/362; 106/189

[56] References Cited
UNITED STATES PATENTS 2,887,440  5/1959  Greminger.......................... 424/362
3,629,237  12/1971  Koyanagi............................ 424/362

Primary Examiner—Theodore Morris
Attorney, Agent, or Firm—Toren, McGeady and Stanger

[57] ABSTRACT

When a mixture comprising 30 to 70% by weight of an enterosoluble cellulose derivative containing a monoester linkage with a polybasic acid, such as, hydroxypropyl methylcellulose phthalate, and 70 to 30% by weight of a digestive fluid-insoluble cellulose derivative, such as, ethylcellulose is used as a coating material for solid medicines, the rate of gradual release of active ingredients of the medicine in the intestinal tracts can be appropriately controlled.

12 Claims, No Drawings

COATING COMPOSITIONS FOR SOLID MEDICINES

FIELD OF THE INVENTION

This invention relates to coating compositions for solid medicines, which are especially suitable for preparation of enterosoluble medicines capable of releasing medicinal ingredients gradually in alimentary canals at controlled rates.

DESCRIPTION OF THE PRIOR ART

Medicines having a durable effect by releasing medicinal active ingredients gradually in alimentary canals have heretofore been prepared by, for example, a method comprising dissolving a water-insoluble material, such as, wax, a synthetic high-molecular compound and a higher aliphatic alcohol in a suitable solvent, adding to the solution a medicine, an excipient, a colorant and other suitable additives, kneading the mixture, granulating the resulting kneaded mixture, optionally incorporating a lubricant or the like into the granules and shaping them into tablets. In such a conventional method, however, since thw water-insoluble material is compounded in a large amount, the resulting medicine becomes extremely massive. Further, some of water-insoluble materials are highly sticky so that it is difficult to perform the mixing operation smoothly, and therefore, in such case coated drugs cannot be prepared conveniently in a commercial scale. Moreover, the slightest variation in the amount of the water-insoluble material added results in a great change in the time required for the release of the active ingredients. In addition to these disadvantages, the above known method are defective in that because the medicinal active ingredients are gradually released also in the stomach, the method cannot be applied to medicines which should be enterosoluble.

There has also been known a method for preparing solid medicines releasing active ingredients gradually, which comprises coating solid medicines with a coating composition comprising a film-forming material which is minimally soluble in digestive fluids (gastric and intestinal fluids) and a material which is easily soluble in the digestive fluids. According to this method, the material easily soluble in digestive fluids is used in an amount of about 5 to about 30% by weight based on the total coating composition. When enterosoluble medicines capable of releasing medicinal active ingredients gradually are prepared according to this known method by employing a film-forming material which is minimally soluble in both the gastric and intestinal fluids and another material soluble in the intestinal fluid, but minimally soluble in the gastric fluid, the resulting coated solid medicines are defective in that all the active ingredients contained in the coated medicines cannot be completely released while they stay in the alimentary canals. This is because the time required for release of the medicinal active ingredients in the intestines is extremely long. Therefore, according to this known method, it is impossible to obtain enterosoluble solid medicines having the desired characteristics of gradual release of the active ingredients.

The specification of U.S. Pat. No. 2,887,440 teaches that a mixture of ethylcellulose and hydroxypropyl methylcellulose can be used as an enteric coating and that when the mixture is used as the enteric coating, the rate of release of the medicinal active ingredients can be easily controlled. However, since hydroxypropyl methylcellulose contained in the mixture is readily soluble in both the gastric and intestinal fluids, in the medicine having a coating of the above mixture, a part of the coating film is dissolved out in the stomach, resulting in dissolution of the active ingredients in the stomach. Further, since the gastric fluid permeates into the medicine through the partially dissolved coating film, there is a fear of decomposition of medicinal components sensitive to the gastric fluid. Therefore, according to this known method, it is impossible to obtain enteric-coated medicines having good characteristics of gradual release of the medicinal ingredients.

SUMMARY OF THE INVENTION

It is therefore a primary object of this invention to provide coating compositions for solid medicines, especially coating compositions suitable for the preparation of enterosoluble solid medicines capable of releasing medicinal active ingredients gradually, which can give a coating which does not dissolve in the gastric fluid and has a high resistance to permeation of the gastric fluid, while dissolving in the intestinal fluid at a suitable rate.

As the result of their strenuous research work, the inventors have found that in solid medicines coated with a mixture of an enterosoluble cellulose derivative having monoester linkages with a polybasic acid and a digestive fluid-insoluble cellulose derivative, if the content of the enterosoluble component in the mixture is at least 30%, preferably at least 40%, a semipermeable film is left undissolved after dissolution of the enterosoluble component in the intestines from the coating layer and this residual film is very effective for controlling the rate of release of the medicinal ingredients contained in the bulk of the medicine and that if the content of the enterosoluble component exceeds 70%, there is a fear that the entire film is disintegrated in the intestines and it is therefore necessary that the content of the enterosoluble component should not exceed 70%, preferably should not exceed 60%.

The enterosoluble cellulose derivatives having monoester linkages with a polybasic acid, which are used in this invention, have a structure in which one of the acid groups of the polybasic acid is combined with the hydroxyl group of the cellulose to form an ester linkage, and these cellulose derivatives are characterized in that they are soluble in organic solvents and intestinal fluid but are insoluble in water and gastric fluid. As far as such solubility characteristics are provided, the kind of the polybasic acid to be used is not particularly critical. Thus, as the enterosoluble cellulose derivatives to be used in this invention, meeting the above solubility requirement, are selected from monoesters of polybasic acids with cellulose ethers, cellulose esters and cellulose ether-esters in which a part or all of hydroxyl groups on the cellulose skeleton are substituted. As the polybasic acid, there can be mentioned, for example, phthalic acid, succinic acid, hexahyurophthalic acid, trimellitic acid, etc. Cellulose deriatives having monoester linkages with such polybasic acid as metioned above can be prepared by using an anhydride of the polybasic acid as the reactant according to known methods.

The enterosoluble cellulose derivatives having such monoester linkages will now be specified with reference to the kinds of substituents and their contents.

a. Hydroxypropyl methylcellulose phthalate:

2-hydroxypropoxyl group $(C_3H_7O_2)$; 4–10% by weight methoxyl group $(CH_3O)$; 18–25% by weight o-carboxybenzoyl group $(C_8H_5O_3)$; 20–35% by weight b. Cellulose acetate phthalate:
   acetyl group $(C_2H_3O)$; 19–23.5% by weight
   o-carboxybenzoyl group $(C_8H_5O_3)$; 30–36% by weight c. Ethylcellulose phthalate:
   ethoxyl group $(C_2H_5O)$; 30–40% by weight
   o-carboxybenzoyl group $(HOOC-C_6H_4-CO)$; 25–30% by weight d. Hydroxypropyl methylcellulose succinate:
   2-hydroxypropoxyl group $(C_3H_7O_2)$; 5–10% by weight
   methoxyl group $(CH_3O)$; 20–24% by weight
   succinyl group $(C_4H_5O_3)$; 20–28% by weight e. Cellulose acetate succinate:
   acetyl group $(C_2H_3O)$; 20–28% by weight
   succinyl group $(C_4H_5O_3)$; 18–28% by weight f. Hydroxypropyl methylcellulose hexahydrophthalate:
   2-hydroxypropoxyl group $(C_3H_7O_2)$; 4–9% by weight
   methoxyl group $(CH_3O)$; 17–21% by weight
   hexahydrophthalyl group $(C_8H_{11}O_3)$; 30–40% by weight g. Cellulose acetate hexahydrophthalate:
   acetyl group $(C_2H_3O)$; 18–24% by weight
   hexahydrophthalyl group $(C_8H_{11}O_3)$; 30–38% by weight h. Hydroxypropyl methylcellulose trimellitate:
   2-hydroxypropoxyl group $(C_3H_7O_2)$; 5–9% by weight
   methoxyl group $(CH_3O)$; 18–22% by weight
   trimellityl group $(C_7H_5O_5)$; 26–33% by weight The digestive fluid-insoluble cellulose derivatives to be used in this invention include cellulose derivatives having a cellulose skeleton, which are soluble in organic solvents but insoluble in both the gastric and intestinal fluids, and as far as cellulose derivatives have such solubility characteristics, the kinds of substituents on the cellulose skeleton are not particularly critical. Accordingly, the digestive fluid-insoluble cellulose derivatives to be used in this invention having the above solubility characterisitcs are selected from cellulose ethers, cellulose esters and cellulose ether-esters in which a part or all of hydroxyl groups on the cellulose skeleton are substituted. In view of the requirement that the cellulose derivatives should be insoluble in both the gastric and intestinal fluids, cellulose derivatives having a small number of hydrophilic substituents are preferably employed. Specific examples of the digestive fluid-insoluble cellulose derivatives to be used in this invention are as follows:

i. Ethylcellulose:
   ethoxy group $(C_2H_5O)$; 44–51% by weight j. Acetylcellulose:
   combined acetic acid group $(C_2H_4O_2)$; 52–62% by weight k. Nitrocellulose:
   nitrogen content (N); 10.5–12.5% by weight l. Cellulose acetate butyrate:
   acetyl group $(C_2H_3O)$; 6–30% by weight
   butyryl group $(C_4H_7O)$; 15–50% by weight m. Cellulose acetate propionate:
   propionyl group $(C_3H_5O)$; 50–58% by weight
   acetyl group $(C_2H_3O)$; 5–15% by weight In this invention it is indispensable to use at least one enterosoluble cellulose derivative and at least one digestive fluid-insoluble cellulose derivative in combination. In the case that one or both the two components are selected from vinyl polymers and acrylic polymers the intended object of this invention cannot be attained. Since the above-specific digestive fluid-insoluble cellulose derivatives to be used in this invention have none of properties causing disadvantages to the coating operation, such as, stickiness and spinnability, a homogeneous coating can be obtained and hence, the semipermeable film left after dissolution of the enterosoluble cellulose derivative is so homogeneous, that the time for release of medicinal ingredients can be controlled accurately and precisely. On the other hand, if the vinyl or acrylic polymer is employed as one of the coating components, the coating operation is difficult and the coating film becomes disintegrated when the enterosoluble component dissolves out in the intestinal fluid, with the result that the intended object of this invention cannot be attained. The reason is considered to be that in the case of a film of a mixture of high-molecular substances differing in their structures, it is impossible to form a homogeneous and tough film.

Coating operation with the coating composition of this invention can be performed according to conventional methods. For instance, the cellulose derivatives selected from the two groups are dissolved into a mixed solvent, consisting of at least one selected from methylene chloride, acetone and ethyl acetate and at least one selected from methanol, ethanol and isopropanol; the resulting solution is incorporated, if necessary with a colorant, a hiding agent, a plasticizer, a flavor and other additives, and the resulting composition is applied on the medicines by a known technique, such as pan coating and fluidizing coating methods. The amounts of the cellulose derivative mixtures to be applied vary depending on the desired properties of the resulting medicines and the desired duration of the medicinal activity, but it is preferably 5 to 50% by weight based on the weight of the solid medicines before coating in the case of granules and 3 to 30% by weight in the case of tablets and pills. In case the amount of the cellulose derivative mixture is smaller than the above, the gastric fluid resistance of the coated medicine is insufficient and such undesired phenomena as disintegration of the coating and release of the medicinal active ingredients in the stomach are apt to occur. The use of the cellulose derivative mixture in an amount exceeding the above range would render the rate of release of the medicinal active ingredients too low, and makes the product uneconomical. In this invention, it is possible to adopt a known method comprising encapsulating several kinds of coated granules differing in the composition and amount of the coating mixture. It is also possible for the coated granules which are shaped into tablets to be incorporated with an excipient, a disinegrating agent, a lubricant or a colorant, if necessary. Furthermore, if desired, the tablets thus formed can be coated with sugar.

The rate of release of the medicinal active ingredients from a medicine coated with the coating composition of this invention can be appropriately controlled by changing the mixing ratio of the enterosoluble cellulose derivative component and the digestive fluid-insoluble cellulose derivative component. This rate can also be adjusted by changing the thickness of the coating. In general, a larger content of the enterosoluble cellulose derivative components results in a shorter time for release of active ingredients.

The coating composition of this invention is applied most effectively to the following cases, for example:

1. Pottasium chloride irritates the stomach and sometimes causes gastric troubles. Further, potassium chloride causes such side effects as vascular pains when a large amount of it is absorbed in the body promptly. It is difficult to maintain a constant level of its concentration in the blood because it is rapidly excreted through the kidneys. Accordingly, in the case of patients requiring the stationary supply of potassium, potassium chloride tablets should be enterosoluble and release potassium chloride gradually in the intestines. Therefore, the coating composition of this invention is effectively used for preparation of enterosoluble potassium chloride medicines of the gradual-release type.

digestive fluid with respect to tablets comprising potassium chloride as the active ingredient which were coated with the coating composition of the invention or comparative coating compositions. The procedure was as follows.

15 Parts of an 8% solution were added to 100 parts of powdery potassium chloride, and the mixture was sufficiently kneaded by the Henschel mixer and granulated by passing it through a sieve No. 20 according to the U.S. standard. The granulated product was airdried at room temperature for 24 hours. The resulting granules were incorporated with 0.5 part of potassium stearate and applied to a rotary tablet machine, to produce tablets, each 9 mm in diameter and 350 mg in weight. 1 kg of the tablets were charged in individual pan coaters, and they were coated with the different coating solutions as indicated in Table 1 by air spray, the coating per tablet being 25 mg in weight.

Table 1

| Component | Formulation A* (parts) | Formulation B** (parts) | Formulation C** (parts) | Formulation D* (parts) | Formulation E* (parts) |
| --- | --- | --- | --- | --- | --- |
| Hydroxypropyl methylcellulose phthalate (grade HP-55 manufactured by Shinetsu Chemical Co.) Hydroxypropoxyl group: 6.8 wt. % Methoxy group. 19.7 wt. % Carboxybenzoyl group: 33.8 wt. % | 20 | 40 | 60 | 80 | |
| Ethylcellulose (grade STD-10 manufactured by Dow Chemical Co.) Ethoxyl group: 49.2 wt. % | 80 | 60 | 40 | 20 | 50 |
| Hydroxy-propyl methylcellulose (grade TC-5 manufactured by Shinetsu Chemical Co.) Hydroxypropoxyl group: 9.2 wt. % Methoxy group: 29.3 wt. % | | | | | 50 |
| Methylene chloride | 450 | 450 | 450 | 450 | 450 |
| Ethanol | 450 | 450 | 450 | 450 | 450 |

* Comparative coating solution
**Coating solution of the present invention

2. Aspirin (trademark for acetylsalicylic acid manufactured by Bayer A. G.) has a stomach-iritating activity and causes gastric troubles and other side effects. Further, it has such an undesired property that when it is absorbed in the body from the alimentary canal, it is excreted from the body in a very short time. Therefore, in order to maintain an appropriate concentration in the blood, it is desired that Aspirin be formed in an enterosoluble medicine releasing the active ingredient gradually. For this purpose, the coating composition of this invention can be effectively used.

This invention will now be illustrated in further detail by reference to the following examples, in which "parts" are all by weight.

EXAMPLE 1

This example was intended to determine the rate of dissolution of potassium chloride into the simulated The coated tablets thus obtained were tested according to Dissolution Test, Method II of the National Formulary (NF) XIII. Procedures not particularly specified in the Formulary were conducted in the following manner.

One coated tablet was placed in each of six tubes of the basket rack assembly. The apparatus was operated for 1 hour using 800 ml of the test solution of the simulated gastric fluid maintained at 37° ± 2°C. as the dissolution fluid. Then, the test solution was replaced by the simulated intestinal fluid, and the same operation was continued for 5 hours. During the test, 5 ml of the dissolution solution was periodically collected and the chloride ion content in the solution was analyzed to determine the ratio of dissolution of potassium chloride from the tablet. The analysis of the chloride ion was conducted according to Mohr's method. The results are shown in Table 2.

Table 2

| Dissolution Fluid | Overall Treating Time (hr.) | Formulation A* (% by weight) | Formulation B** (% by weight) | Formulation C** (% by weight) | Formulation D* (% by weight) | Formulation E* (% by weight) |
|---|---|---|---|---|---|---|
| Simulated gastric fluid test solution | 1 | 0 | 0 | 0 | 0 | 38.2 |
| Simulated intestinal fluid test solution | 2 | 1.9 | 12.3 | 21.6 | 99.7 | 76.8 |
| ditto | 3 | 4.6 | 41.8 | 51.9 | — | 98.1 |
| ditto | 4 | 7.8 | 79.7 | 89.8 | — | 99.3 |
| ditto | 5 | 12.5 | 99.0 | 99.6 | — | — |

* Comparative coating solution
** Coating solution of the present invention

In formulation E above, the enterosoluble cellulose derivative polybasic acid monoester of this invention was replaced by a cellulose derivative soluble in both the gastric and intestinal fluids. In this case, potassium chloride was dissolved out in the simulated gastric fluid test solution. Therefore, it is apparent that when this coated tablet is orally administered, the dissolution of potassium chloride is caused to occur in the gastric fluid, and hence, the intended object of this invention would not be attained. In the case of formulation A, the rate of dissolution of potassium chloride was so low that there was a possibility that all of the active ingredient was not completely absorbed in the body and a part of it was eliminated outside the body without absorption. In the case of formulation D, the dissolution rate was too high and hence, the coated tablet did not exhibit a long durability. Therefore, it was not suitable for attaining the object of this invention.

Since the residence time of food or the like in the small intestines is generally 4 to 5 hours, it is apparent that the coated tablets prepared with use of formulation B or C of this invention are very effective and suitable as enteric coated tablets of the gradual release type.

EXAMPLE 2

Coated tablets were prepared in the same manner as in Example 1 by employing the following coating solution, and they were tested in the same manner as in Example 1.

| Formulation A | |
|---|---|
| Cellulose acetate phthalate (CAP manufactured by Wako Junyaku Co., Ltd.) | 55 parts |
|    Acetyl group : 20.1 wt. % | |
|    Carboxybenzoyl group : 35.1 wt. % | |
| Ethylcellulose (grade STD-10 manufactured by Dow Chemical Company) | 45 parts |
|    Ethoxyl group : 49.2 wt. % | |
| Dibutyl phthalate | 20 parts |
| Methylene chloride | 600 parts |
| Ethanol | 400 parts |
| Formulation B | |
| Hydroxypropyl methylcellulose phthalate (grade HP-50 manufactured by Shinetsu Chemical Co.) | 50 parts |
|    Hydroxypropoxy group : 7.9 wt. % | |
|    Methoxy group : 23.1 wt. % | |
|    Carboxybenzoyl group : 22.3 wt. % | |
| Acetylcellulose (grade M-AC manufactured by Daicel, Ltd. : degree of acetylation (combined acetic acid group) = 54.9 wt. %) | 50 parts |
| Triacetin | 10 parts |
| Acetone | 800 parts |
| Methanol | 200 parts |
| Formulation C | |
| Hydroxypropyl methylcellulose hexahydrophthalate | 58 parts |
|    Hydroxypropoxyl group : 5.6 wt. % | |
|    Methoxyl group : 18.3 wt. % | |
|    Hexahydrophthalyl group : 38.2 wt. % | |
| Cellulose acetate butyrate | 42 parts |
|    Acetyl group : 21.2 wt. % | |
|    Butyryl group : 25.5 wt. % | |
| Triacetin | 20 parts |
| Acetone | 900 parts |
| Ethanol | 100 parts |
| Formulation D | |
| Ethylcellulose phthalate | 57 parts |
|    Ethoxyl group : 33.2 wt. % | |
|    Carboxybenzoyl group : 26.8 wt. % | |
| Cellulose acetate propionate | 43 parts |
|    Acetyl group : 54.3 wt. % | |
|    Propionyl group : 8.2 wt. % | |
| Triacetin | 20 parts |
| Acetone | 800 parts |
| Ethanol | 200 parts |

The results of the potassium chloride dissolution test made on coated tablets prepared with use of these formulations are shown in Table 3.

Table 3

| Dissolution Fluid | Overall Treating Time (hr.) | Formulation A (%) | Formulation B (%) | Formulation C (%) | Formulation D (%) |
|---|---|---|---|---|---|
| Simulated gastric fluid test solution | 1 | 0 | 0 | 0 | 0 |
| Simulated intestinal fluid test solution | 2 | 14.8 | 23.4 | 18.2 | 14.1 |
| ditto | 3 | 39.5 | 59.1 | 52.6 | 38.1 |
| ditto | 4 | 79.8 | 85.2 | 78.6 | 83.6 |
| ditto | 5 | 99.5 | 99.3 | 99.8 | 99.9 |

EXAMPLE 3

20 parts of a 8% solution of gelatin was added to 100 parts of powdery potassium chloride, and the mixture was sufficiently kneaded well by the Henschel mixer. The kneaded mixture was extruded to form granules by an extrusion granulator equipped with a screen plate having holes of 1.0 mm in diameter. The granulated product was dried at 50°C. for 6 hours by a mechanical convection drying oven. Then, 4 kg of the granules thus obtained were charged in a fluidizing coater (Model WSG-5 of Glatt Company, West Germany) and coated with the coating solution indicated below:

Coating Solution Composition

| | |
|---|---|
| Hydroxypropyl methylcellulose phthalate (grade HP-50 manufactured by Shinetsu Chemical Co.) Hydroxypropoxyl group : 7.9 wt. % Methoxyl group : 23.1 wt. % Carboxybenzoyl group : 22.3 wt. % | 40 parts |
| Ethylcellulose (grade STD-10 manufactured by Dow Chemical Company) Ethoxyl group : 49.2 wt. % | 32 parts |
| Methylene chloride | 600 parts |
| Ethanol | 400 parts |

Five kinds of coated granules which were different in the amount of coating, i.e., 8, 13, 20, 30 and 45% by weight based on the weight of granules before the coating operation, were prepared and were mixed together in equal amounts. The resulting mixture was filled in hard gelatin capsules in an amount of 500 mg per capsule. The rate of dissolution of potassium chloride from the so prepared capsules was tested in the same manner as described in Example 1 to obtain the results shown in Table 4.

Table 4

| Dissolution Fluid | Overall Treating Time (hr.) | Ratio of Dissolution of Potassium Chloride (% by weight) |
|---|---|---|
| Simulated gastric fluid test solution | 1 | 0 |
| Simulated intestinal fluid test solution | 2 | 24.8 |
| ditto | 3 | 49.1 |
| ditto | 4 | 78.0 |
| ditto | 5 | 99.8 |

EXAMPLE 4

Since Aspirin irritates the stomach and causes such side effects as gastric troubles, it is usually administered in the form of an enteric coated tablet. However, Aspirin has the a property that once it is absorbed in the body through the alimentary canals, it is promptly eliminated from the body through the kidneys. Accordingly, in order to maintain an appropriate concentration in blood, it is desired that Aspirin is administered in the form of an enteric coated medicine of the gradual release type. This example illustrates how the coating composition of this invention is suitable for formation of such Aspirin tablets.

A mixture of 80 parts of Aspirin and 20 parts of lactose was incorporated with a 15% solution of polyvinyl pyrrolidone in isopropanol, and the mixture was well kneaded by the Henschel mixer. The kneaded mixture was extruded to form granules by an extrusion granulator equipped with a screen plate having holes of 1.0 mm in diameter. The granules were dried at 50°C for 6 hours in a mechanical convection drying oven. The granules thus obtained were coated with a coating solution indicated in Table 5 by a fluidizing coater (Model WSG-5 of Glatt Company, West Germany). The amount of coating as solid was 15% by weight based on the weight of the granule before the coating operation in very case.

Table 5

| Components | Formulation A (parts) | Formulation B (parts) | Formulation C (parts) | Formulation D (parts) | Formulation E (parts) |
|---|---|---|---|---|---|
| Cellulose acetate phthalate (CAP manufactured by Wako Junyaku Co., Ltd.) Acetyl group: 20.1 wt. % Carboxybenzoyl group: 35.1 wt.% | 18 | 24 | 30 | 36 | 42 |
| Ethylcellulose (grade STD-10, manufactured by Dow Chemical Co.) Ethoxy group: 49.2 wt. % | 42 | 36 | 30 | 24 | 13 |
| Dibutyl phthalate | 15 | 15 | 15 | 15 | 15 |
| Methylene chloride | 600 | 600 | 600 | 600 | 600 |
| Ethanol | 400 | 400 | 400 | 400 | 400 |

All of the coated granules with the coating solutions of Formulations A to E were mixed together in equal amounts, and the resulting mixture was put into hard gelatin capsules in an amount of 500 mg per capsule. The dissolution of the thus capsulated Aspirin was tested in the same manner as in Example 1 with the following modification.

The analysis of Aspirin was conducted by filtering the sample solution through a filter paper, diluting 1 ml of te filtrate with a buffer solution (pH = 1.3) of KCl—HCl so that the volume of the dilution was 50 ml and determining the ultraviolet absorption by using the original dissolution fluid as a control solution. Since Aspirin was partially hydrolyzed during this treatment and converted to salicylic acid, the dissolution rate of Aspirin was calculated based on both the amounts of Aspirin and salicylic acid. The contents of Aspirin and salicylic acid were determined by absorbances at maximum absorption wavelengths of 278 m$\mu$ and 303 m$\mu$, respectively. The results are shown in Table 6.

Table 6

| Dissolution Fluid | Treating Time (hr.) | Dissolution Ratio of Aspirin (% by weight) |
|---|---|---|
| Simulated gastric fluid test solution | 1 | 0 |
| Simulated intestinal fluid test solution | 2 | 21.1 |
| ditto | 3 | 58.5 |
| ditto | 4 | 87.6 |
| ditto | 5 | 99.8 |

What is claimed is:

1. A coating composition for a solid medicine comprising (1) an enterosoluble cellulose derivative having monoester linkages with a polybasic acid the amount of polybasic acid groups being from 20–40% by weight based on the cellulose derivative and (2) a digestive fluid-insoluble cellulose derivative, the mixing ratio of component (1) with component (2) being 30–70% by weight to 70–30% by weight.

2. The coating composition was claimed in claim 1 wherein said mixing ratio of component (1) with component (2) is 40–60% by weight to 60–40% by weight.

3. The coating composition as claimed in clain 1 wherein said component (1) is at least one selected from the group consisting of hydroxypropyl methylcellulose phthalate, cellulose acetate phthalate, ethylcellulose phthalate, hydroxypropyl methylcellulose succinate, cellulose acetate succinate, hydroxypropyl methylcellulose hexahydrophthalate, cellulose acetate hexahydrophthalate and hydroxypropyl methylcellulose trimellitate.

4. The coating composition as claimed in claim 1 wherein said component (2) is at least one selected from the group consisting of ethylcellulose, acetylcellulose, nitrocellulose, cellulose acetate butyrate and cellulose acetate propionate.

5. The coating composition as claimed in claim 1 wherein said component (1) is hydroxypropylmethylcellulose phthalate and said component (2) is ethylcellulose.

6. The coating composition as claimed in claim 1 wherein said component (1) is cellulose acetate phthalate and said component (2) is ethylcellulose.

7. The coating composition as claimed in claim 1 wherein said component (1) is hydroxypropyl methylcellulose phthalate and said component (2) is acetylcellulose.

8. The coating composition as claimed in claim 1 wherein said component (1) is hydroxypropyl methylcellulose hexahydrophthalate and said component (2) is cellulose acetate butyrate.

9. The coating composition as claimed in claim 1 wherein said component (1) is ethylcellulose phthalate and said component (2) is cellulose acetate propionate.

10. The coating composition as claimed in claim 1 wherein said coating composition is dissolved in a mixed solvent comprising at least one selected from the group consisting of methylene chloride, acetone and ethyl acetate and at least one selected from the group consisting of methanol, ethanol and isopropanol.

11. A method for preparing an enterosoluble medicine comprising coating a solid medicine with the coating composition of claim 1.

12. A method for preparing an enterosoluble medicine comprising coating a solid medicine with the coating composition of claim 10.

* * * * *